United States Patent [19]

Flatland

[11] 3,962,788

[45] June 15, 1976

[54] DENTAL HANDPIECE

[76] Inventor: Lloyd P. Flatland, 15 Quisisana Drive, Kentfield, Calif. 94904

[22] Filed: Jan. 4, 1974

[21] Appl. No.: 430,742

[52] U.S. Cl. .................................................. 32/27
[51] Int. Cl.² ........................................... A61C 1/10
[58] Field of Search ................................. 32/26, 27

[56] References Cited
UNITED STATES PATENTS

| | | | |
|---|---|---|---|
| 3,101,542 | 8/1963 | Fodor | 32/27 |
| 3,325,899 | 6/1967 | Staunt | 32/27 |
| 3,499,223 | 3/1970 | Lieb et al. | 32/27 |

Primary Examiner—Robert Peshock
Attorney, Agent, or Firm—Lothrop & West

[57] ABSTRACT

A dental handpiece has a preferably spherical housing in which a pair of ball bearings are mounted with the exterior races of the bearings against the housing and the interior races of the bearings aligned on an axis. Mounted on the two inner bearing races is a hollow spindle accessible through axial openings in the housing on the opposite ends of the spindle. The spindle has an interior taper and interior threads. Fitting into the spindle is a hollow chuck tube having an exterior taper fitting the interior taper and having exterior threads fitting the interior threads. All of the threads are of only partial depth. One end of the chuck tube has a flange abutting a bearing interior race and has a wrench-receiving portion. The other end of the spindle also has a wrench-receiving portion.

1 Claim, 7 Drawing Figures

DENTAL HANDPIECE

It is of interest to provide a dental handpiece having a head that is small and compact so that it occupies very little room in the patient's mouth, yet which serves as a good support for the rotating dental tool. It is also of interest to provide a handpiece in which the mechanism for receiving the dental tool is highly accurate, affords a firm grip and can readily be manipulated by the dentist when it is necessary to change the working tool.

Another requirement of a dental handpiece is that it be relatively simple mechanically and easily, economically and accurately made.

It is therefore an object of the invention to accomplish all of the foregoing aims in a satisfactory fashion.

Another object of the invention is to provide a dental handpiece that can be utilized with presently standard dental tools and will handle them in an easy and improved fashion.

A further object of the invention is in general to provide a greatly improved dental handpiece.

Other objects, together with the foregoing, are attained in the embodiment of the invention described in the accompanying description and illustrated in the accompanying drawings, in which.

Figure 1:
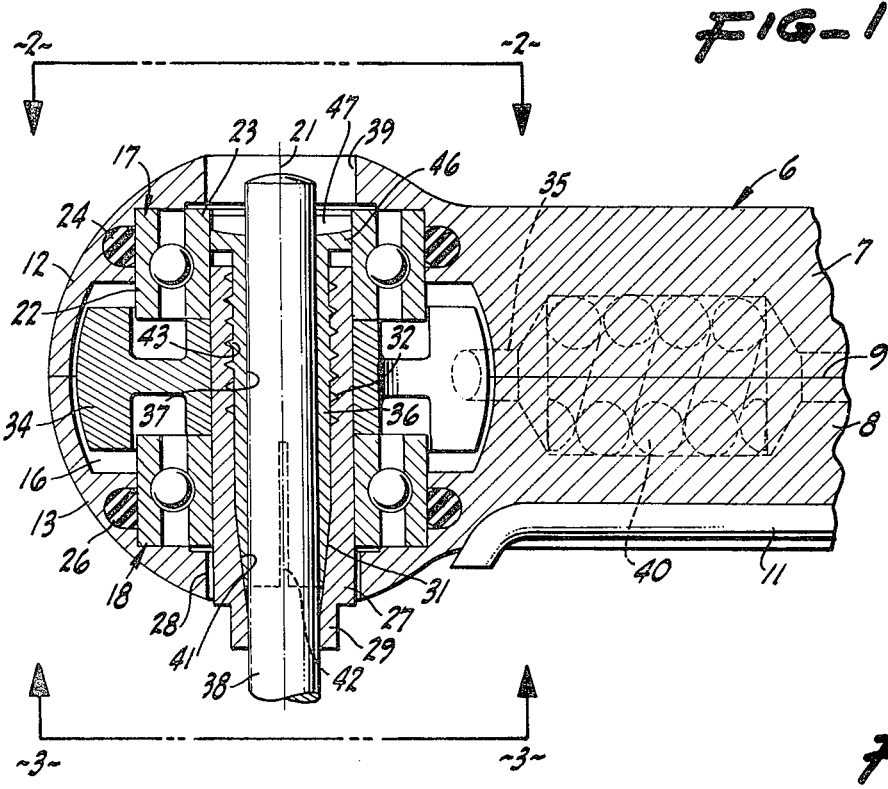
FIG. 1 is a cross-section on a longitudinal, axial plane through a dental handpiece constructed pursuant to the invention, some portions being broken away to reduce the size of the figure.
Figure 2:
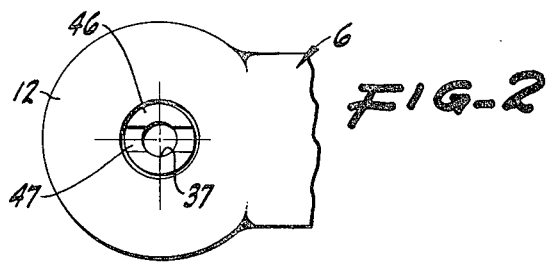
FIG. 2 is a view of the structure of FIG. 1 from above and to a reduced scale.
Figure 3:
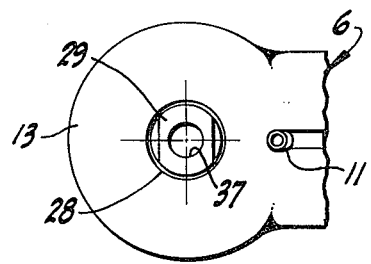
FIG. 3 is a view of the structure of FIG. 1 from below and to the same scale as FIG. 2.
Figure 4:
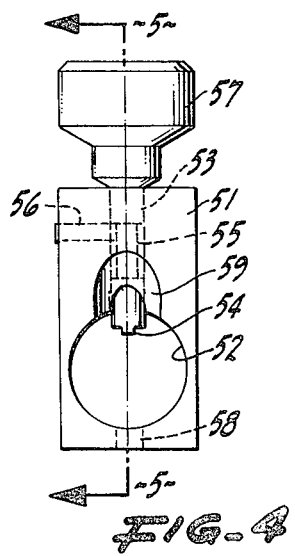
FIG. 4 is an end view of a tool for use with the structure of FIG. 1.
Figure 5:
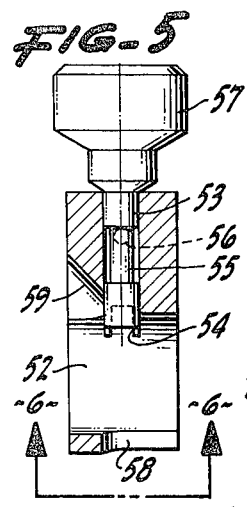
FIG. 5 is a cross-section of the tool shown in FIG. 4, the plane of section being indicated by the line 5—5 of FIG. 4.
Figure 6:
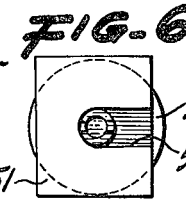
FIG. 6 is a bottom view of the tool of FIG. 5 taken on the plane 6—6 of FIG. 5.
Figure 7:
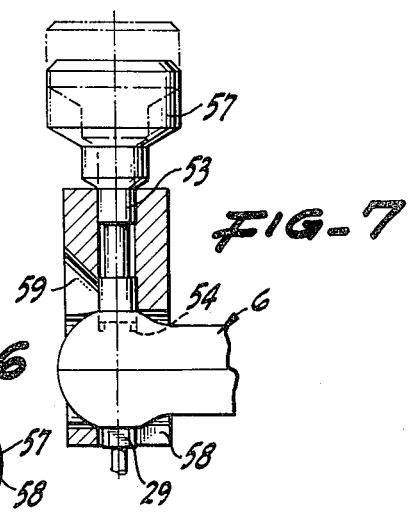
FIG. 7 is a cross-section comparable to FIG. 5 but showing parts of the tool in a different location and in position on the dental handpiece.

While the dental handpiece can be incorporated in a widely variant number of ways, it has with practical success been embodied as shown herein. The handpiece in general is of the same type as shown in my copending application entitled "Dental Handpiece" filed Oct. 27, 1972 with Ser. No. 301,263 issued as Pat. No. 3,858,323 on Jan. 7, 1975 and to which reference is made for portions of the handpiece not shown in detail herein.

The handpiece includes a grip portion 6 made up of an upper section 7 and a lower section 8 meeting on a transverse median plane 9 and secured together by any suitable means, not shown. The lower section 8 carries a tube 11 for cooling water in the standard way. The two sections 7 and 8 at one extremity are formed into hemispheres 12 and 13 which together make up a spherical housing defining or enclosing an interior chamber 16.

In the upper member 12, as well as in the lower member 13, there are disposed bearings 17 and 18 in alignment on a through axis 21. Each of the bearings is preferably a ball bearing and includes an outer race 22 as well as an inner race 23. The outer races are each slightly spaced radially from the housing and are disposed against cushions 24 and 26, which conveniently are elastomeric O-rings seated in receiving grooves in the housing.

Adapted to be received in the housing and to be carried by the aligned inner races 23 is a hollow spindle 27 extending through the inner race 23 of the lower bearing 18 and also extending through an axial opening 28 in the housing half 13. The hollow spindle at its lower end projects through the opening 28 and has a non-circular portion 29 effective or shaped; for example, by flats to receive a wrench of a standard kind. Within the hollow spindle the configuration near the lower end is that of a cone 31 having an appropriate taper, whereas the upper portion of the spindle adjacent the other end thereof is provided with internal threads 32 of a standard form but not of full depth. The threads rather are partial threads so that the grooves forming part of the threads are spaced by circular-cylindrical portions of the interior surface of the spindle. The upper end of the spindle, although entering into and well seated in the inner race 23, so as to be guided thereby, nevertheless stops short of extending through the race.

The spindle arrangement so described is utilized as the support for an air turbine wheel 34 having opposite, annular, undercut portions and adapted to receive driving air through a duct 35 in the grip portion, as described in the above-noted application, there being a wick oiler 40 in the duct.

Designed to enter into the hollow spindle is a chuck tube 36 which has an interior bore 37 of appropriate configuration to receive the shank 38 of a standard dental tool. The shank extends virtually through the housing and occupies a position in an axial opening 39 in the upper portion thereof, so as to be easily accessible. The chuck tube at its lower end has a taper 41 matching the taper 31 and likewise has an axial split 42 or several comparable axial splits, although one is presently preferred. The upper portion of the chuck tube has exterior partial threads 43 designed to interengage with the threads 32. Between the threads 43 are circular-cylindrical portions which abut the comparable circular-cylindrical portions of the spindle. In this way the parts are placed in good positioning relationship without relying upon full threads to afford a concentric fit.

At its upper end the chuck tube is enlarged to afford a flange 46 extending radially to a circular-cylindrical exterior rim which seats against the interior of the inner race 23 of the bearing 17. Furthermore, the upper end of the chuck tube is provided with a cross slot 47 in the flange affording a wrench-engaging portion accessible through the opening 39.

In operation, with the parts in position as shown in FIG. 1, the turbine wheel 34 is rotated rapidly and so rotates the spindle, the chuck tube and any tool which is in the chuck tube. The spindle and tube are held in appropriate alignment by the inner races of the ball bearings as well as by the cone, the flange and the partial threads. The bearings, in turn, are held in alignment through the cushion rings 24 and 26. There is thus afforded a well-aligned, concentric mounting for high-speed operation.

When the tool is to be changed, the hollow spindle is held and the chuck tube is rotated relative thereto to back off the interengaged tapers so that the chuck tube can expand slightly, releasing its grip on the tool shank. In the event it is difficult to dislodge the tool, the end thereof is accessible through the opening 39 so that it can be easily forced out. A new tool can then be inserted, whereupon the hollow spindle is again held and an appropriate tool in engagement with the chuck tube relatively rotates the chuck tube. This drives it into the spindle and contracts the tapered portion by reducing the split 42, thus gripping the shank of the tool.

To assist in the relative rotation of the hollow spindle and of the chuck tube, there is preferably afforded a special tool, as shown in FIGS. 4–7 inclusive. This tool is a block 51 which has a circular-cylindrical bore 52 extending therethrough from side to side and of a diameter easily to receive the spherical housing 12. Mounted in the block is a stem 53 at its lower end having a special, hollow, driver-like formation 54 designed to operate in the sides of the slot 47 whether or not a tool shank passes therethrough. The stem 53 is provided with a reduced portion 55 into which a transverse pin 56 in the body extends to limit the axial movement of the stem 53. At its upper end, the stem is substantially enlarged and constitutes a thumb and finger knob 57 so that the stem can be manually rotated.

In use, the handpiece is introduced into the opening 52. There is a narrow slot 58 cut into the body 51 in order to receive the extended portion 29 of the spindle and to pass the extended portion of a tool 38 which may be in the spindle. The sides of the slot 58 are positioned so that they closely engage the flats 29 on the hollow spindle and so prevent such spindle from rotating, the tool itself being restrained by the grip portion 6. When the handpiece end is being introduced into the opening 52, the knob 57 is withdrawn to an upper position, shown in broken lines in FIG. 7, thus taking the driver portion 54 out of the opening 52 and permitting the spherical end to be appropriately positioned. As soon as the handpiece is in position, the knob 57 is moved into its lower position, as shown in full lines in FIG. 7, with the tool portion 54 thereof in engagement with the walls of the slot 47. An inspection groove 59 in the body makes the interengagement of the driver 54 and of the slot 47 easily visible.

When the knob 57 is then rotated relative to the block 51, the chuck tube is correspondingly rotated with regard to the hollow spindle. Rotation of the knob in opposite directions causes tightening or loosening of the chuck tube with respect to the tool. When the desired result has been accomplished, the handpiece is removed from the body 51 and is available for operation.

What is claimed is:

1. A dental handpiece comprising:

a housing having an opening therethrough and having a pair of bearings mounted therein in alignment on an axis extending along said opening and adjacent opposite ends of said opening each of said bearings having a rotatable inner race;

a hollow spindle rotatably carried by said inner races, extending through one of said inner races and outwardly of said housing at one end of said opening and terminating at its other end between the ends of the other inner race, said spindle having an interior taper portion and interior threads;

a chuck tube having an exterior taper portion engaging said interior taper and external threads engaging said internal threads, said chuck tube having a cylindrical bore of uniform diameter completely therethrough and terminating at one end in a flange extending outwardly thereof adjacent said other end of said hollow spindle and between said ends of the other inner race; and tool engaging means on said flange outwardly of said bore.

* * * * *